United States Patent [19]

Iida et al.

[11] 4,216,308

[45] Aug. 5, 1980

[54] FORTIMICIN FACTORS D AND KE COMPOUNDS

[75] Inventors: Takao Iida, Tokyo; Kunikatsu Shirahata; Isao Matsubara, both of Machida; Masahiro Sugimoto; Shinzo Ishii, both of Shizuoka; Ryo Okachi, Machida; Takashi Nara, Tokyo, all of Japan

[73] Assignee: Abbott Laboratories, North Chicago, Ill.

[21] Appl. No.: 974,434

[22] Filed: Dec. 29, 1978

Related U.S. Application Data

[62] Division of Ser. No. 845,970, Oct. 27, 1977, Pat. No. 4,145,253.

Foreign Application Priority Data

Oct. 28, 1976 [JP] Japan .................................. 51-128837
Jan. 14, 1977 [JP] Japan .................................... 52-2338

[51] Int. Cl.² ...................... A61K 31/71; C07H 15/22
[52] U.S. Cl. ................................ 536/17 R; 424/180; 424/181; 435/80
[58] Field of Search .......................................... 536/17

[56] References Cited

U.S. PATENT DOCUMENTS

| | | | |
|---|---|---|---|
| 3,878,193 | 4/1975 | Reimann | 536/17 |
| 3,963,695 | 6/1976 | Cooper et al. | 536/17 |
| 4,091,032 | 5/1978 | Tadanier et al. | 536/17 |
| 4,124,756 | 11/1978 | Martin et al. | 536/17 |

*Primary Examiner*—Johnnie R. Brown
*Attorney, Agent, or Firm*—Fitzpatrick, Cella, Harper & Scinto

[57] ABSTRACT

New antibiotic compounds, Fortimicin factors D and KE are produced by fermentation of microorganisms belonging to the genus Micromonospora. The antibiotic compounds are accumulated in the culture liquor and are isolated therefrom. A semisynthetic method of producing Fortimicin KE utilizing Fortimicin D is also disclosed.

3 Claims, 6 Drawing Figures

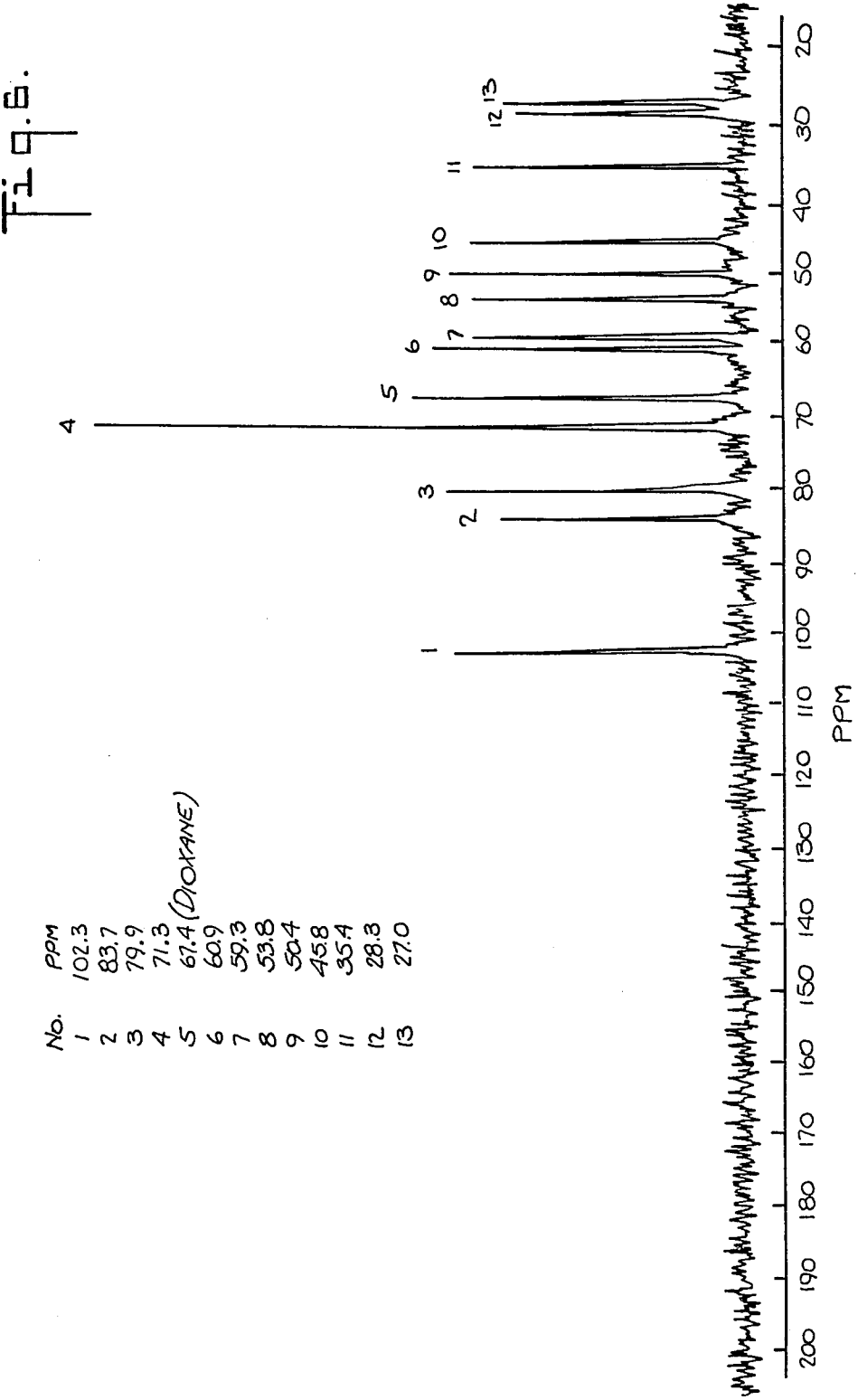

FORTIMICIN FACTORS D AND KE COMPOUNDS

This is a division of application Ser. No. 845,970 filed Oct. 27, 1977, now U.S. Pat. No. 4,145,253.

RELATED APPLICATIONS

The present invention is related generally to the inventions disclosed in U.S. Pat. No. 3,931,400 issued Jan. 6, 1976 for Fortimicin B and Process for Production Thereof; U.S. Pat. No. 3,976,768 issued Aug. 24, 1976 for Fortimicin A and Process For Production Thereof; and U.S. Pat. No. 4,048,015 issued Sept. 13, 1977 for Fortimicin C and Process for Production Thereof.

BACKGROUND OF THE INVENTION

The present invention relates to new compositions of matter having antibacterial properties having the general formula I:

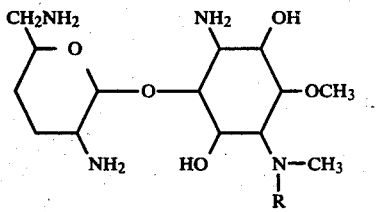

[wherein R is H (Fortimicin KE) or

(Fortimicin D)]

The invention also pertains to the production of Fortimicin D and/or Fortimicin KE by culturing a microorganism belonging to the genus Micromonospora, which is capable of producing one or both of the active substances in a nutrient medium, until antibacterial activity is detected in the culture liquor and then isolating at least one of the active substances therefrom.

Antibiotics which exhibit activity against a broad spectrum of bacteria are always in demand. To this end, it has been found that when certain strains of Micromonospora are cultured in a nutrient medium, several antibiotic substances are produced in the culture liquor. Specifically, Fortimicin factors A, B and C have been isolated from the culture liquor of *Micromonospora olivoasterospora* Mk-70 (ATCC 21819) (FERM-P No. 1560) and have the following structural formulae:

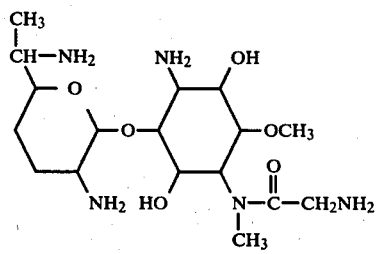

The chemical, physical and biological properties of these antibiotics and the processes for the production thereof are explained in detail in the specifications of the aforementioned United States Patents.

It has now been found that *Micromonospora olivoasterospora* MK-70, when cultured, liberates two further active substances other than Fortimicin A, Fortimicin B and Fortimicin C. A study of the chemical, physical and biological properties of these active substances indicates that the compositions of matter are new antibiotics which have now been named Fortimicin D and Fortimicin KE.

SUMMARY OF THE INVENTION

In accordance with the present invention, novel antibiotics having the general formula I, Fortimicin factors D and KE, are produced by fermentation of a microorganism belonging to the genus Micromonospora, which is capable of producing one or both of said factors, in a nutrient medium until substantial antibacterial activity is detected in the culture liquor. At the completion of culturing, the active fractions containing Fortimicin D or Fortimicin KE are isolated from the culture liquor by known means such as by ion exchange resin treatment.

Fortimicin D and KE exhibit broad antibacterial activity, and are, therefore, useful inter alia to clean and sterilize laboratory glassware and surgical instruments, and may also be used in combination with soaps, detergents and wash solutions for sanitation purposes. Further, Fortimicin D is expected to be used as therapeutic compound on various infections (in human beings and in animals) induced by various bacteria.

Included in the composition of matter aspect of the invention are the pharmaceutically acceptable non-toxic acid addition salts of Fortimicin D and Fortimicin KE including the mineral acid addition salts such as hydrochloride, hydrobromide, hydroiodide, sulfate, sulfamate and phosphate and the organic addition salts such as maleate, acetate, citrate, oxalate, succinate, benzoate, tartrate, fumarate, malate, mandelate, ascorbate and the like.

DETAILED DESCRIPTION OF THE INVENTION

Figure 1:
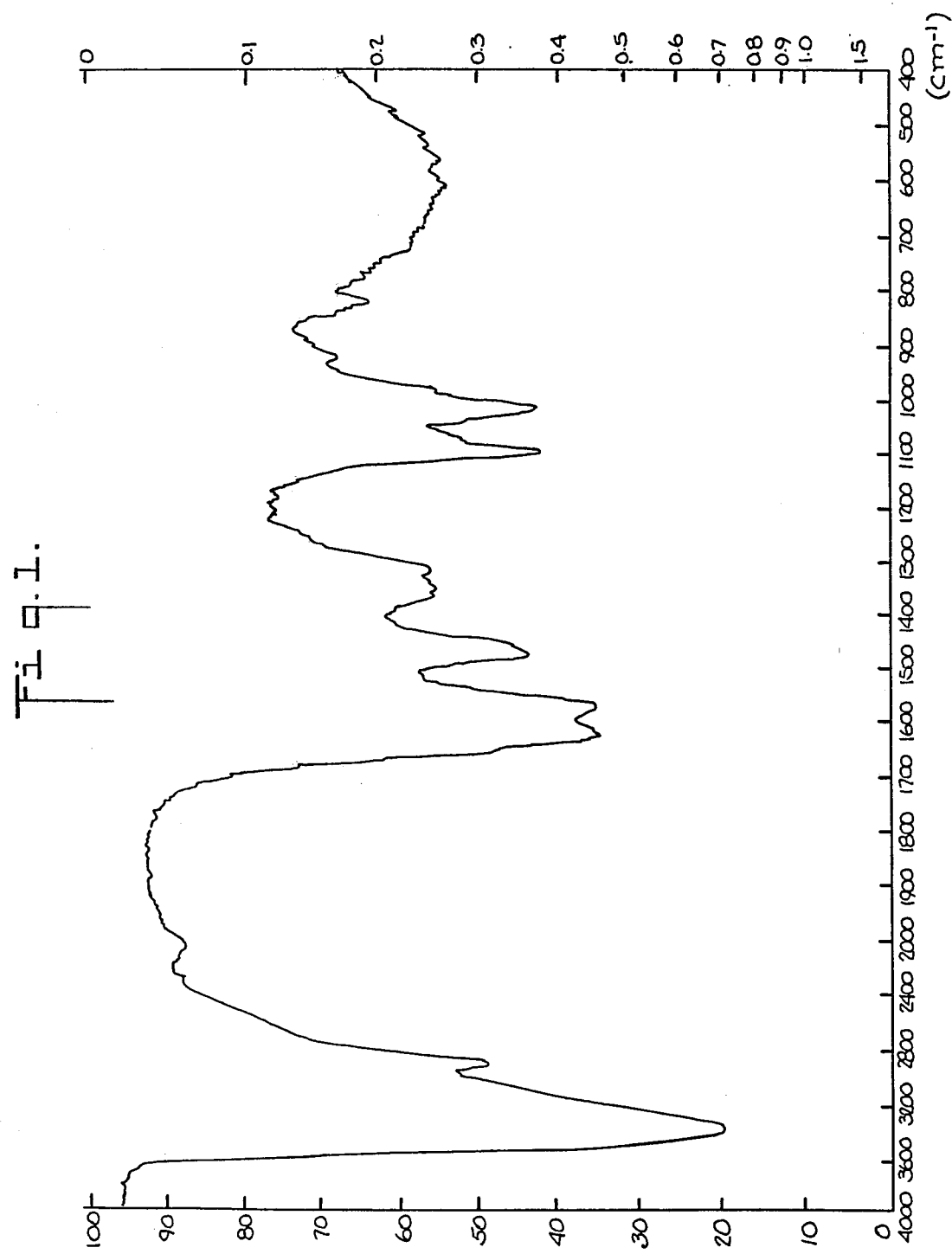
Figure 2:
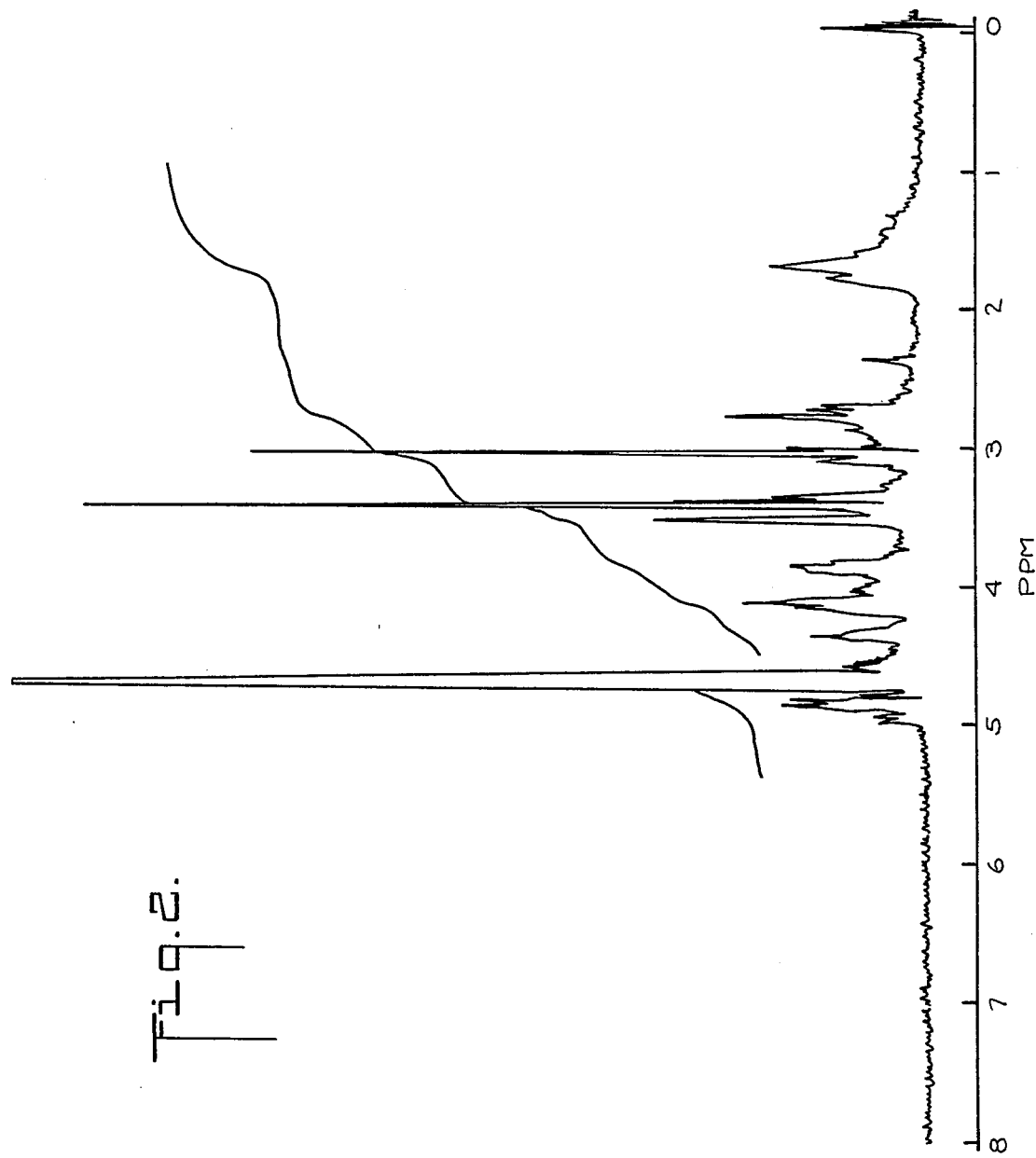
Figure 3:
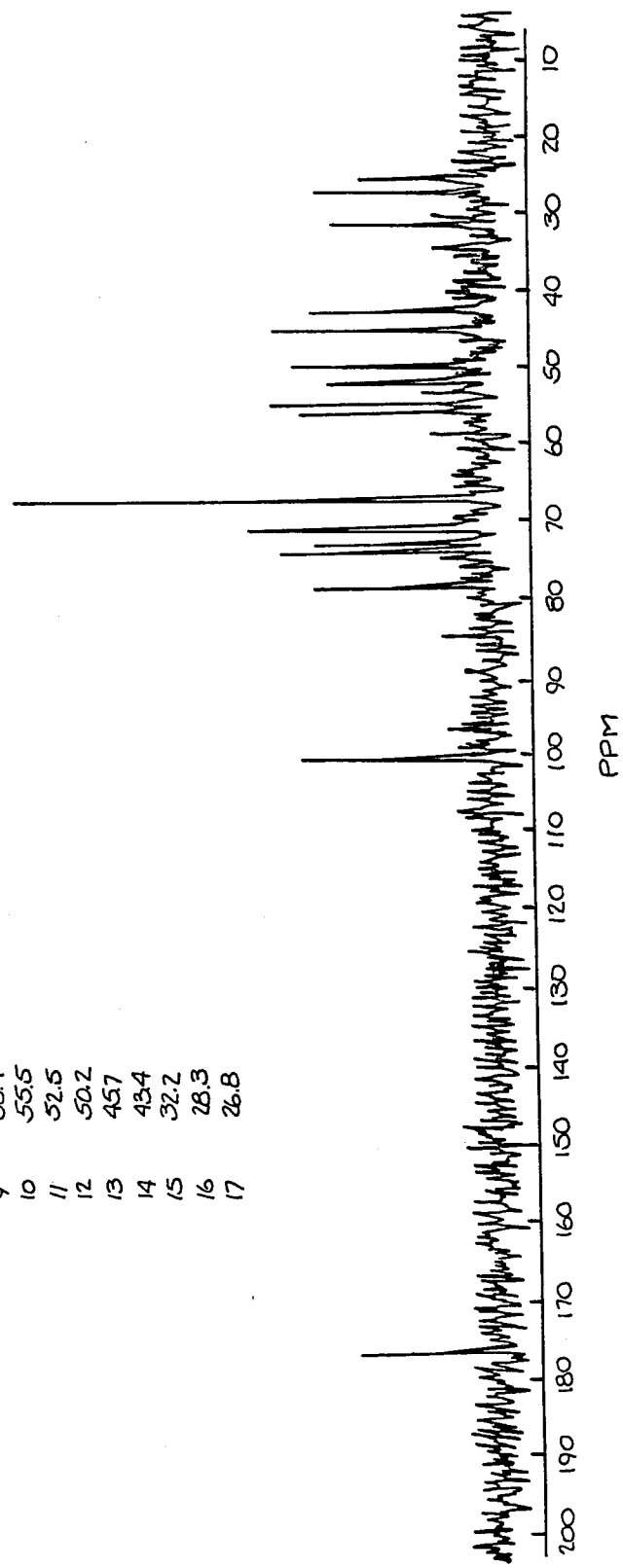
Figure 4:
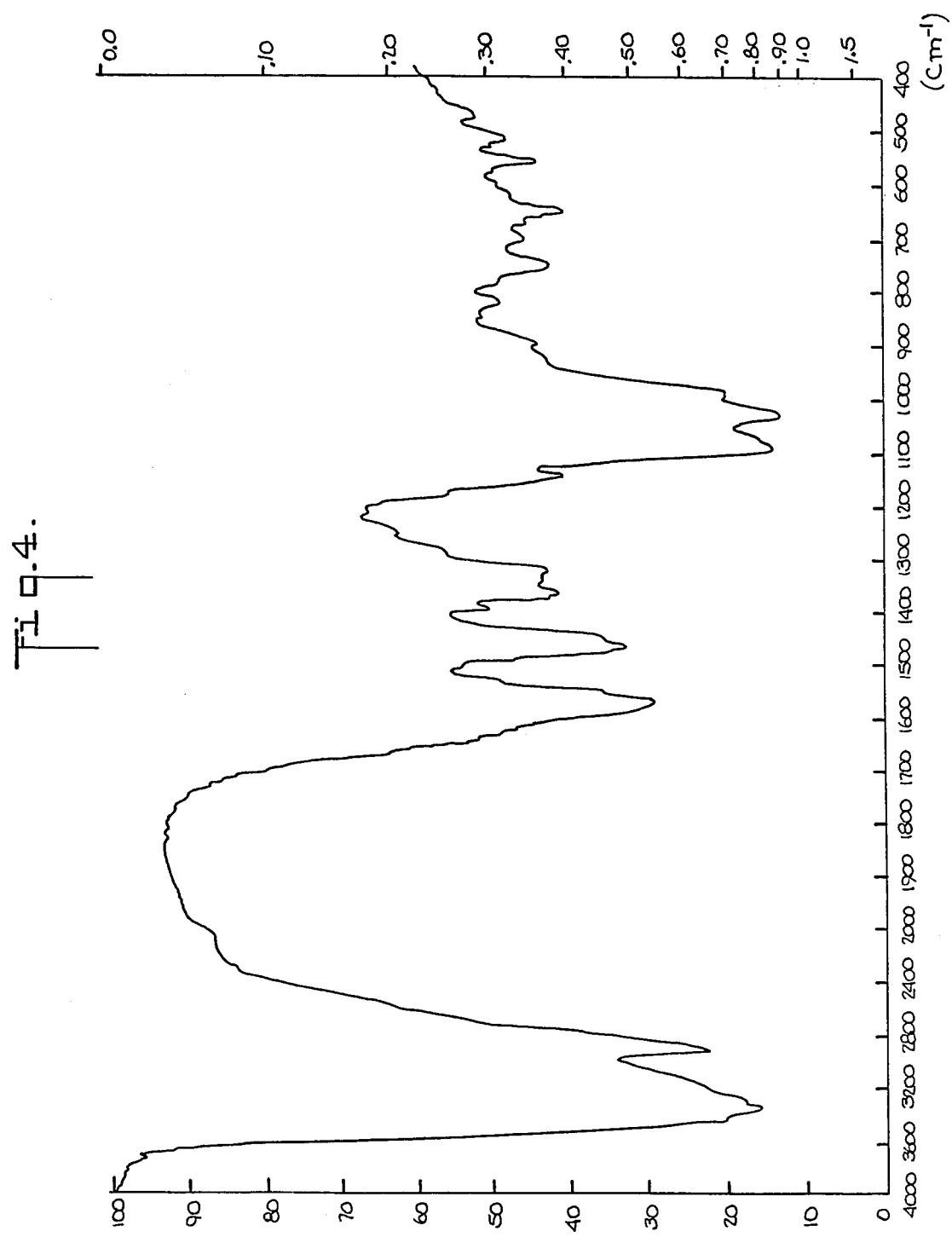
Figure 5:
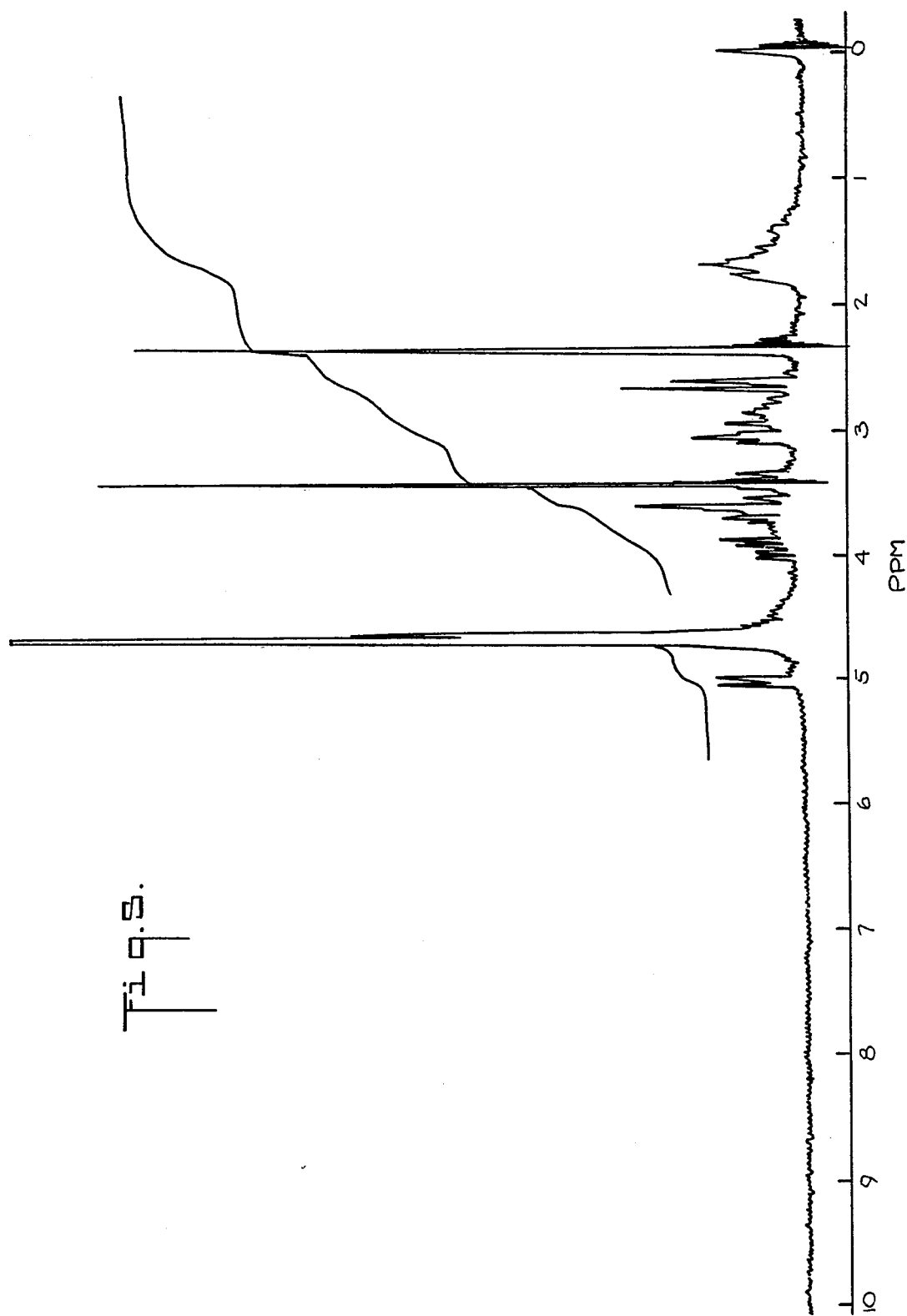

The physicochemical properties of the free base of Fortimicin D of the present invention are as follows:

(1) A basic white powder (2) The elementary analytical value found:
C=44.15%, H=8.77%, N=15.86%

(3) Melting point: 109°-114° C.

(4) Ultraviolet absorption spectrum: Ultraviolet absorption spectrum of an aqueous solution of the substance does not show characteristic maximum absorption between 220 nm and 360 nm but only shows terminal absorption.

(5) Specific rotation: $[\alpha]_D^{25} = +121°$ (C=0.5, $H_2O$)

(6) Infrared absorption spectrum: The infrared absorption spectrum is measured in KBr tablet. The free base of Fortimicin D shows maximum absorption at the following wavenumbers ($cm^{-1}$): 3400, 2900, 1625, 1570, 1470, 1350, 1315, 1020

(7) Color reactions:

Ninhydrin reaction: positive

Potassium permanganate reaction: positive

Elson-Morgan's reaction: negative

Biuret reaction: negative (8) The PMR spectrum of Fortimicin D is measured in a deuterium oxide solution (pD=10.1) by using JEOL JNM-PS-100.

The results are as follows: δ 1.10–1.90(4H, m), 2.50–3.06(4H, m), 3.07(3H, s), 3.45(3H, s), 3,53(2H, s), 3.70–4.25(4H, m), 4.36(1H, t, J=3.0), 4,88(1H, d, J=4.0), 4.92(1H, d,d, J=3.0,9.0)

(9) The CMR specturm of Fortimicin D is measured in a deuterium oxide solution (pD=11.1) by using JEOL-PFT-100A.

The results are as follows: δ 176.5, 100.1, 78.5, 73.6, 73.0, 71.3, 71.1, 56.4, 55.5, 52.5, 50.2, 45.7, 43.4, 32.2, 28.3, 26.8.

(10) The mass spectrum of the substance reveals the following M+1 ion and fragment ions. The formula in parentheses means the composition formula obtained by high resolution mass spectrometry.

| m/e | | |
|---|---|---|
| 392 | M + 1 ($C_{16}H_{34}N_5O_6$) | |
| 374 | ($C_{16}H_{30}N_4O_6$), | 292 ($C_{11}H_{22}N_3O_6$), |
| 274 | ($C_{11}H_{20}N_3O_5$), | 264 ($C_{10}H_{22}N_3O_5$), |
| 246 | ($C_{10}H_{20}N_3O_4$), | 235 ($C_9H_{19}N_2O_5$), |
| 207 | ($C_8H_{19}N_2O_4$), | 129 ($C_6H_{13}N_2O$) |

From the result of the mass spectrometry, the molecular weight of the substance is determined to be 391 and the molecular formula is determined to be $C_{16}H_{33}N_5O_6$. The elementary analytical values of the substance (hydrated with 2.5 moles of $H_2O$) as calculated from the molecular formula are C=44.01%, H=8.79% and N=16.04%.

(11) Based on the foregoing physicochemical data, the structural formula of Fortimicin D is considered to be as follows:

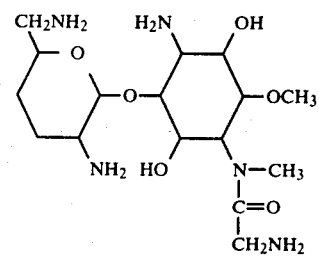

(12) The free base of Fortimicin D is readily soluble in water, soluble in methanol and slightly soluble in ethanol and acetone but is insoluble in organic solvents such as chloroform, benzene, ethyl acetate, butyl acetate, ethyl ether, butanol, petroleum ether, n-hexane, etc.

The physicochemical properties of the free base of Fortimicin KE of the present invention are as follows:

(1) A basic white powder (2) The elementary analytical value found: C=48.18%, H=9.29%, N=15.84%

(3) Melting point: 72°-77° C.

(4) Ultraviolet absorption spectrum: Ultraviolet absorption spectrum of an aqueous solution of the substance does not show characteristic maximum absorption between 220 nm and 360 nm but only shows terminal absorption.

(5) Specific rotation: $[\alpha]_D^{25} = +28.5°$ (C=0.5, $H_2O$)

(6) Infrared absorption spectrum: The infrared absorption spectrum is measured in KBr tablet. The free base of Fortimicin KE shows maximum absorption at the following wavenumbers ($cm^{-1}$): 3350, 2920, 1580, 1470, 1370, 1330, 1090, 1035

(7) Color reactions:

Ninhydrin reaction: positive

Potassium permanganate reaction: positive

Elson-Morgan's reaction: negative

Biuret reaction: negative (8) The PMR spectrum of Fortimicin KE is measured in a deuterium oxide solution (pD=11.1) by using JEOL JNM-PS-100.

The results are as follows: δ 1.10–1.90(4H, m), 2.40(3H, s), 2.66(2H, d, J=6.0), 2.69–3.20(3H, m), 3.48(3H, s), 3.49(1H, t, J=9.5), 3.59–4.10(3H, m), 3.92(1H, d,d, J=4.5,9.5), 5.04(1H, d, J=4.0)

(9) The CMR spectrum of the substance is measured in a deuterium oxide solution (pD=11.0) by using JEOL PFT-100A.

The results are as follows. δ 102.3, 83.7, 79.9, 71.3, 71.3, 71.3, 60.9, 59.3, 53.8, 50.4, 45.8, 35.4, 28.3, 27.0.

(10) The mass spectrum of the substance reveals the following M+1 ion and fragment ions. The formula in parentheses means the composition formula obtained by high resolution mass spectrometry.

| m/e | | |
|---|---|---|
| 335 | M + 1 ($C_{14}H_{31}N_4O_5$) | |
| 317 | ($C_{14}H_{27}N_3O_5$), | 235 ($C_9H_{19}N_2O_5$), |
| 207 | ($C_8H_{19}N_2O_4$), | 189 ($C_8H_{17}N_2O_3$). |
| 129 | ($C_6H_{13}N_2O$) | |

From the result of the mass spectrometry, the molecular weight of the substance is determined to be 334 and the molecular formula is determined to be $C_{14}H_{30}N_4O_5$. The elementary analytical values of the substance (hydrated with 1 mole of $H_2O$) as calculated from the molecular formula are C=47.71%, H=9.15% and N=15.89%.

(11) Based on the foregoing physicochemical data, the structural formula of Fortimicin KE is considered to be as follows:

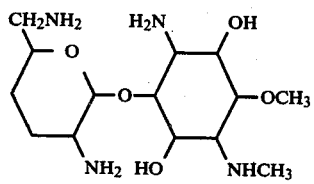

(12) The free base of Fortimicin KE is readily soluble in water, soluble in methanol and slightly soluble in ethanol and acetone but is insoluble in organic solvents such as chloroform, benzene, ethyl acetate, butyl acetate, ethyl ether, butanol, petroleum ether, n-hexane, etc.

The Rf values of Fortimicin D and Fortimicin KE in paper chromatography and thin layer chromatography using various developers are shown in the following tables 1 to 3. For comparison, the Rf values of antibiotics similar to Fortimicin D and KE are also given.

Table 1

The Rf values of Fortimicin D and Fortimicin KE in ascending paper chromatography (at 28° C.

| Developer | Rf value-D | Rf Value-KE | Period of development (hours) |
|---|---|---|---|
| 20% ammonium chloride | 0.96 | 0.96 | 3 |
| water-saturated n-butanol | 0.00 | 0.00 | 15 |
| n-butanol.acetic acid.water (3:1:1) (by volume) | 0.06 | 0.06 | 15 |
| water-saturated ethyl acetate | 0.00 | 0.00 | 4 |
| water-saturated n-butanol containing 2% (W/V) p-toluene sulfonic acid and 2% (W/V) piperidine | 0.04 | 0.04 | 15 |

Table 2

The Rf values in silica gel thin layer chromatography (at room temperature after three hours of development)

| Developer* | Antibiotic | Rf value |
|---|---|---|
| I | Fortimicin D | 0.74 |
| " | Fortimcin KE | 0.78 |
| " | Fortimicin A | 0.74 |
| " | Fortimicin B | 0.80 |
| " | Fortimicin C | 0.75 |
| " | Gentamicin complex | 0.71 |
| " | Gentamicin C$_{1a}$ | 0.71 |
| " | Sisomicin | 0.71 |
| II | Fortimcin D | 0.37 |
| " | Fortimicin KE | 0.58 |
| " | Fortimicin A | 0.37 |
| " | Fortimicin B | 0.62 |
| " | Fortimicin C | 0.40 |
| " | Gentamicin complex | 0.06–0.16 |
| " | Gentamicin C$_{1a}$ | 0.16 |
| " | Sisomicin | 0.18 |

*Developer I: The upper layer of chloroform, methanol and 17% (w/w) aqueous ammonia (2:1:1 by volume).
Developer II: 10% ammonium acetate and methanol (1:1 by volume).

Table 3

The Rf values of various antibiotics in ascending paper chromatography using the lower layer of chloroform, methanol and 17% (w/w) aqueous ammonia (2:1:1 by volume) as the developer (at room temperature; after 12 hours of development).

| Antibiotics | Rf value |
|---|---|
| Streptomycin A | 0.02 |
| Streptomycin B | 0.00 |
| Bluensomycin | 0.01 |
| Ribostamycin | 0.00 |
| Lividomycin A | 0.00 |
| Lividomycin B | 0.03 |
| Hygromycin B | 0.02 |
| Lividomycin D | 0.02 |
| Spectinomycin | 0.45 |
| Kasugamycin | 0.01 |
| Butirosine A | 0.00 |
| Butirosine B | 0.01 |
| Gentamicin A | 0.00 |
| Gentamicin B | 0.00 |
| Gentamicin C$_{1a}$ | 0.18 |
| Gentamicin C$_1$ | 0.59 |
| Gentamicin C$_2$ | 0.38 |
| Sisomicin | 0.18 |
| Neomycin A | 0.00 |
| Neomycin B | 0.03 |
| Antibiotic No. 460 | 0.01 |
| Neomycin C | 0.00 |
| Kanamycin A | 0.02 |
| Kanamycin B | 0.01 |
| Kanamycin C | 0.02 |
| Paromomycin | 0.00 |
| Nebramycin complex | 0.01 |
| Tobramycin | 0.02 |
| Apramycin | 0.02 |
| Nebramycin factor 4 | 0.01 |
| Nebramycin factor 5 | 0.00 |
| Myomycin | 0.00 |
| XK-62-2* | 0.49 |
| Fortimicin B | 0.65 |
| Fortimicin A | 0.37 |
| Fortimicin C | 0.18 |
| Fortimicin D | 0.18 |
| Fortimicin KE | 0.59 |

*an antibiotic disclosed in U.S. Pat. No. 4,045,298.

Table 4 illustrates the antibacterial spectra of Fortimicin D and Fortimicin KE against various microorganisms.

Table 4

(minimum Inhibitory Concentration, γ/ml measured by agar dilution method at pH 8.0)

| Microorganism | Fortimicin D γ/m | Fortimicin KE γ/ml |
|---|---|---|
| Bacillus subtilis No. 10707 | 0.02 | 104.2 |
| Staphylococcus aureus ATCC 6538P | 0.02 | 1.65 |
| Klebsiella pneumoniae ATCC 10031 | 0.08 | 26.1 |
| Escherichia coli ATCC 26 | 0.32 | 26.1 |
| Escherichia coli KY 8315 | 0.13 | 26.1 |
| Escherichia coli Ky 8327 (resistant to kanamycin, gentamicin and tobramycin) | 0.13 | 26.1 |
| Pseudomonas aeruginosa BMH No. 1 | 5 | 208.3 |
| Pseudomonas aeruginosa KY 8510 (resistant to kanamycin, kanamycin B, tobramycin, gentamicin C$_{1a}$ and ribostamycin) | 5 | — |
| Shigella sonnei ATCC 9290 | 0.3 | 26.1 |
| Salmonella typhosa ATCC 9992 | 0.08 | 13.1 |

As is apparent from the above, Fortimicin D has a strong antibacterial activity against a broad range of Gram-positive and Gram-negative bacteria. Particularly, it is characteristic that the antibiotic is effective against certain strains of Escherichia coli which are resistant to kanamycin, gentamicin and tobramycin. Further, Fortimicin D is expected to have a therapeutic effect on various infections (in human beings and in animals) induced by the above-mentioned various bacteria. In this regard, the $LD_{50}$ of Fortimicin D sulfate for dd-mouse weighing $20\pm1$ g. has been determined to be 159 mg/kg. With such antibacterial properties, Fortimicin D is applicable to medicinal purposes. As is also apparent from the above, Fortimicin KE exhibits a broad antibacterial spectrum. Further, Fortimicin KE has a merit of being stable in an alkaline solution.

A comparison of Fortimicin factors D and KE with known antibiotics further illustrates their novelty. As water-soluble, basic antibiotics produced by microorganisms of the genus Micromonospora and having a broad range of antibacterial spectra, there are the gentamicin complex (M. J. Weinstein et al: Antimicrobial Agents and Chemotherapy, 1963, 1; D. J. Cooper et al: J. Infect Dis. 119, 342, 1969; and J. A. Waitz et al: Antimicrobial Agents and Chemotherapy 2, 464, 1972), antibiotic No. 460 (Japanese Patent Publication No. 46-16153), sisomicin (M. J. Weinstein et al: J. Antibiotics, 23, 551, 555, 559, 1970), XK-62-2 (U.S. Pat. No. 4,045,298), Fortimicin B, Fortimicin A and Fortimicin C. As shown in the above Table 3, gentamicin A, B, $C_2$ and $C_1$ components show Rf values of 0.00, 0.00, 0.38 and 0.59, respectively in the paper chromatography. On the other hand, in the same paper chromatography, the Rf value of Fortimicin D is 0.18 and of Fortimicin KE is 0.59. Thus, Fortimicin D is clearly different from the gentamicin components and Fortimicin KE is different from all except gentamicin $C_1$. In the paper chromatography of Table 3, Fortimicin D shows the same RF value (0.18) as that of gentamicin $C_{1a}$ (0.18) and therefore Fortimicin D and gentamicin $C_{1a}$ can not be distinguished from each other in this respect. However, in the silica gel thin layer chromatography of Table 2 using the developer II, Fortimicin D (Rf value: 0.37) is clearly distinguished from gentamicin $C_{1a}$ (Rf value: 0.16). Similarly in Table 2, gentamicin $C_1$, $C_2$ and $C_{1a}$ show Rf values of 0.06 to 0.16 whereas Formicin KE shows an RF value of 0.58. Comparing Fortimicin factors D and KE with antibiotic No. 460, sisomicin, XK-62-2, Fortimicin B, Fortimicin A and Fortimicin C, as is apparent from Table 3, antibiotic No. 460, sisomicin, XK-62-2, Fortimicin B, Fortimicin A and Fortimicin C show Rf values of 0.01, 0.18, 0.49, 0.65, 0.37 and 0.18 respectively. The Rf value of Fortimicin D is 0.18 and of Fortimicin KE is 0.59. Fortimicin KE is thus clearly different. Although the Rf value of Fortimicin D is the same (in Table 3) as sisomicin and Fortimicin C, in the silica gel thin layer chromatography in Table 2 using the developer II, Fortimicin C (Rf value: 0.40) and sisomicin (Rf value: 0.18) are clearly distinguished from Fortimicin D (Rf value: 0.37).

In addition, as water-soluble, basic antibiotics produced by Actinomycetes other than those of the genus Micromonospora and having a broad antibacterial spectra, streptomycin A and B, ribostamycin, lividomycin A, B and D, spectinomycin, kasugamicin, neomycin A, B and C, kanamycin A, B and C, nebramycin complex, nebramycin factors 4 and 5 and paromomycin may be mentioned. Fortimicin factors D and KE have been found to be greatly different from any of these antibiotics in physicochemical properties. Moreover, as is apparent from Table 3, Fortimicin factors D and KE are quite different from these antibiotics in the Rf values in the paper chromatography.

From the foregoing, Fortimicin factors D and KE are considered to be a new antibiotics.

Fortimicin D and KE are produced by fermentation of a microorganism belonging to the genus Micromonospora. Any strain belonging to the genus Micromonospora and capable of forming Fortimicin D and/or Fortimicin KE in the culture liquor may be used. Examples of preferred strains are Micromonospora olivoasterospora MK-70 (FERM-P No. 1560) (ATCC 21819), Micromonospora olivoasterospora MK-80 (FERM-P No. 2192) (ATCC 31010) and Micromonospora olivoasterospora Mm 744 (FERM-P No. 2193) (ATCC 31009). These strains have been deposited with the American Type Culture Collection, Rockville, Maryland, U.S.A. and with the Fermentation Research Institute Agency of Industrial Science and Technology, Tokyo, Japan and have been accorded the accession numbers noted above.

The microbiological properties of these strains are described in U.S. Pat. No. 3,931,400, which description is expressly incorporated herein by reference.

As is the case with other strains of Actinomycetes, the microorganisms useful in carrying out the present invention can be mutated by artificial means such as ultraviolet irradiation, X-ray irradiation and use of various mutation including chemicals in known manner to enhance the production of metabolic products, an example of which is Micromonospora olivoasterospora CS-26 (FERM-P No. 3567, NRRL 8178). This latter mutant has been deposited with the United States Department of Agriculture, Peoria, Illinois, and is freely available to the public.

Generally, conventional methods for culturing Actinomycetes may be employed in the process of the present invention. Thus, various nutrient sources may be used for the culture medium. Appropriate carbon sources include glucose, starch, mannose, fructose, sucrose, molasses, etc. either alone or in combination. Hydrocarbons, alcohols, organic acids, etc. may also be used depending upon the assimilability possessed by the microorganisms to be used. As inorganic and organic nitrogen sources, ammonium chloride, ammonium sulfate, urea, ammonium nitrate, sodium nitrate, may be used either alone or in combination or natural nitrogen sources such as peptone, meat extract, yeast extract, dry yeast, corn steep liquor, soybean powder, casamino acid, soluble vegetable protein, etc. are appropriate. If necessary, inorganic salts such as sodium chloride, potassium chloride, calcium carbonate, phosphates, etc. may be added to the medium. Moreover, organic and inorganic materials which promote the growth of the particular strain and the production of Fortimicin factors D and/or KE may be added.

A liquid culturing method, particularly a submerged stirring culturing method is most suitable. Culturing temperature is desirably 25°–40° C., and it is preferred to carry out culturing at around neutral pH. Usually, after 2 to 15 days of liquid culturing, Fortimicin D and Fortimicin KE are formed and accumulated in the culture liquor. When the yield of the antibiotics in the culture liquor reaches a maximum, culturing is discontinued and the desired product is isolated and purified from the culture liquor after the microbial cells have been removed such as by filtration.

Isolation and purification of Fortimicin D and Fortimicin KE is carried out by methods usually used for the isolation and purification of microbial metabolic products from a culture liquor.

Since the antibiotics Fortimicin D and Fortimicin KE are basic substances and are readily soluble in water but poorly soluble in the ordinary organic solvents, the antibiotics can be purified by the methods usually used for the purification of so-called water-soluble basic antibiotics. More specifically, the D and KE factors can be purified by a proper combination of absorption and desorption from cation exchange resin, cellulose column chromatography, adsorption and desorption using a column of Sephadex LH-20, silica gel column chromatography, etc. As an example, a suitable method of purification of Fortimicin D from the culture liquor when a strain capable of producing the Fortimicin complex (a mixture containing Fortimicin A, B, C, D and KE and by-products having antibacterial activity) is used is as follows. The cell-free culture filtrate is adjusted to pH 7.5 and is then flowed through a cation exchange resin such as Amberlite IRC-50 (ammonium form) (Rohm & Haas Co., U.S.A.). After the resin is washed with water, elution is carried out with 0.5 N aqueous ammonia. The active fractions are combined and concentrated under reduced pressure. The concentrate is then treated with an anion exchange resin, Dowex 1×2 (OH form) (The Dow Chemical Co., U.S.A.). The active fractions obtained by the elution are combined and concentrated under reduced pressure to obtain a crude powder of Fortimicin complex. The crude powder is dissolved in water and the solution is then adjusted to a pH of 5.0 1 with 2 N sulfuric acid and then is passed through a column packed with active carbon to adsorb the active principles. The column of active carbon is then washed with water to remove impurities. Thereafter, elution is carried out with 0.2 N sulfuric acid to elute the active principles. The active fractions are combined and, after neutralization with an anion exchange resin such as Dowex 44 (OH form) (The Dow Chemical Co., U.S.A.), are freeze-dried to obtain free base of the Fortimicin complex.

In the case of the Fortimicin complex containing Fortimicin D, the crude powder of Fortimicin complex obtained above is subjected to silica gel column chromatography using a mixed solvent of isopropanol, chloroform and concentrated aqueous ammonia (4:2:1 by volume) as a developer. The crude powder is suspended in the solvent and introduced into the column. Development is carried out with the same solvent at a flow rate of about 30 ml/hour. First, Fortimicin B is eluted and after several trace components are eluted, Fortimicin A is eluted in large active fractions. Then, elution is continued and after Fortimicin C is eluted, Fortimicin D is eluted in the next large active fractions. The active fractions containing Fortimicin D are collected and concentrated under reduced pressure. The concentrate is freeze-dried to obtain a white-colored free base of Fortimicin D. In this manner, a considerably purified sample of Fortimicin D can be obtained by silica gel column chromatography. However, sometimes some impurities are present in the sample. In this case, the sample is further subjected to cellulose column chromatography. As the developer, a mixed solvent of n-butanol, pyridine, acetic acid and water (6:4:2:4 by volume) is used. The active fractions obtained by elution are combined and concentrated under reduced pressure to obtain a purified preparate of Fortimicin D. For the removal of impurities showing positive reaction with ninhydrin, column chromatography using carboxymethylcellulose is also effective. More specifically, in this case, a solution of the crude powder is passed through a column packed with carboxymethylcellulose (ammonium form). The active principles are adsorbed on the carboxymethylcellulose. Then, the column is thoroughly washed with water to elute most of the pigments and inorganic salts. Thereafter, elution is carried out with 0.2 N ammonium bicarbonate to elute the active principles. Fractions containing Fortimicin D are combined and freeze-dried to obtain purified Fortimicin D.

During the above-described purification procedures, the fractions are checked by silica gel thin layer chromatography. As the developer, a mixed solvent of isopropanol, chloroform, and concentrated aqueous ammonia (2:1:1 by volume) is used and development is carried out at room temperature for 2 hours. Fortimicin D shows an Rf value of about 0.43 on the silica gel thin layer chromatogram.

In the case of the Fortimicin complex containing Fortimicin KE and Fortimicin D, the crude powder obtained by freeze-drying is dissolved in water. After being adjusted to pH 7.5 with 2 N sulfuric acid, the solution is passed through a column packed with a cation exchange resin, Amberlite CG-50 type I (ammonium form) (produced by Rohm & Haas Co., U.S.A.) to adsorb the Fortimicin complex thereon. The column is then washed with water. Thereafter, elution is carried out with 0.2 N aqueous ammonia. After several trace components are eluted, a mixture of Fortimicin B and Fortimicin KE is eluted in large active fractions. Then, after several trace components are eluted, Fortimicin A and Fortimicin D are eluted. Active fractions containing Fortimicin KE and Fortimicin B are combined and dried to obtain a powder of free bases of Fortimicin KE and Fortimicin B. Thereafter, the powder is subjected to silica gel column chromatography using a mixed solvent of isopropanol, chloroform and concentrated aqueous ammonia (4:2:1 by volume) as a developer. The powder mentioned above is suspended in the mixed solvent and the suspension is introduced into a column packed with silica gel. Development is carried out with the same solvent at a flow rate of about 30 ml/hour. The active fractions eluted first is Fortimicin B. Thereafter, Fortimicin KE is eluted. The fractions containing Fortimicin KE are combined and concentrated under reduced pressure. The concentrate is dissolved in a small amount of water and freeze-dried to obtain the free base of Fortimicin KE. In this manner, a considerably purified sample of Fortimicin KE can be obtained by silica gel column chromatography. However, sometimes some impurities are present in the sample. If desired to obtain Fortimicin D from the active fractions containing Fortimicin D and Fortimicin A, the similar procedure using silica gel chromatography mentioned before can be used.

During the above-described purification procedures, the fractions are checked by silica gel thin layer chromatography. As the developer, a mixed solvent of isopropanol, chloroform and concentrated aqueous ammonia (2:1:1 by volume) is used and development is carried out at room temperature for 2 hours. Fortimicin KE shows an Rf value of about 0.58 on the silica gel thin layer chromatogram.

Fortimicin KE may also be obtained by heating Fortimicin D in an alkaline aqueous solution such as sodium hydroxide and barium hydroxide. Specifically, Fortimicin D is heated in an aqueous solution of saturated barium hydroxide at a temperature of 100° C. for 3 hours. Then the reaction solution is neutralized with dry ice and the resulting precipitate of barium carbonate is removed by filtration. The filtrate is concentrated and passed through a column packed with Amberlite CG-50 (ammonium form). After washing the column with water, elution is carried out with 0.2 N aqueous ammonia. First, a small amount of reaction by-products is eluted and subsequently Fortimicin KE is eluted. The fractions containing Fortimicin KE are combined and concentrated under reduced pressure. The concentrate is then freeze-dried to obtain the free base of Fortimicin KE.

Certain specific embodiments of the present invention are illustrated by the following representative examples.

EXAMPLE 1

A. Culturing of the CS-26 strain

*Micromonospora olivoasterospora* CS-26 (NRRL 8178) (FERM-P No. 3567) is used as the seed strain. The seed strain is a mutant strain derived from *Micromonospora olivoasterospora* MK-70 (ATCC 21819) (FERM-P No. 1560) by means of treatment with nitrosoguanidine, ultraviolet irradiation and $\gamma$-ray irradiation. A medium comprising 2 g/dl glucose, 0.5 g/dl peptone, 0.5 g/dl yeast extract and 0.1 g/dl calcium carbonate (pH 7.5 before sterilization) is used as a first seed medium. A loopful of the seed strain is inoculated into 10 ml portions of the first seed medium in 50 ml-large test tubes and is cultured at 30° C. for 5 days. Then, 10 ml of the thus prepared first seed culture is inoculated into 30 ml portions of a second seed medium in 250 ml-Erlenmeyer flasks. The second seed medium has the same composition as that of the first seed medium. The second seed culturing is carried out with shaking at 30° C. for 2 days, and thereafter, 30 ml of the second seed culture is inoculated into 300 ml portions of a third seed medium in 2 l-Erlenmeyer flasks provided with baffles. The third seed medium is of the same composition as that of the first seed medium. The third seed culturing is carried out with shaking at 30° C. for 2 days. Then, 1.5 l of the third seed culture (corresponding to 5 flasks) is inoculated into 15 l of a fourth seed medium in a 30 l-stainless steel jar fermenter. The fourth seed medium has the same composition as that of the first seed medium. The fourth seed culturing in the jar fermenter is carried out with aeration and stirring (revolution: 350 r.p.m.; aeration: 15 l/min) at 37° C. for 2 days. Then, 15 l of the fourth seed culture is inoculated into 150 l of a fermentation medium in a 300 l-fermenter. The fermentation medium has the following composition:

| Soluble starch | 4 g/dl | $K_2HPO_4$ | 0.05 g/dl | $CaCO_3$ | 0.1 g/dl |
| --- | --- | --- | --- | --- | --- |
| Soybean meal | 2 g/dl | $MgSO_4 . 7H_2O$ | 0.05 g/dl | | |
| Corn steep liquor | 1 g/dl | KCl | 0.03 g/dl | | |

(pH 7.5 before sterilization)

Fermentation in the fermenter is carried out with aeration and stirring (revolution: 150 r.p.m.; aeration: 80 l/min) at 37° C. for 4 days.

B. Isolation of crude Fortimicin complex

After the completion of fermentation, the culture liquor is adjusted to pH 2.5 with concentrated sulfuric acid and is stirred for 30 minutes. Thereafter, about 7 kg of a filter aid, Radiolite No. 600 (product of Showa Kagaku Kogyo Co., Ltd.) is added to the culture liquor and the microbial cells are removed by filtration. The filtrate is adjusted to pH 7.5 by the addition of 6 N sodium hydroxide, and then passed through a column packed with about 20 l of a cation exchange resin, Amberlite IRC-50 (ammonium form). The active principles are adsorbed on the resin, and the effluent is discarded. After the resin is washed with water, elution of the active principles is carried out with 0.5 N aqueous ammonia. The eluate is subjected to determination of activity by a paper disc method using an agar plate of *Bacillus subtilis* No. 10707. Fractions showing an activity are combined and concentrated under reduced pressure to about 1 L. The concentrate is then passed through a column packed with 500 ml of an anion exchange resin, Dowex 1×2 (OH form) and then about 2 L of water is passed through the column. In this manner, impurities are removed and the active principles are eluted with water. The active fractions are combined and concentrated under reduced pressure to about 100 ml. The concentrate is passed through a column packed with about 50 ml of active carbon powder whereby the active principles are adsorbed. The column is washed with water and the effluent and washings are discarded. Elution is carried out with 0.2 N sulfuric acid. The eluate is subjected to determination of activity by a paper disc method using *Bacillus subtilis* No. 10707. The active fractions are combined and passed through a column of a resin, Dowex 44 (OH form) and elution of the active principles is carried out with water. The active fractions are combined and concentrated to about 50 ml. The concentrate is freeze-dried to obtain a crude powder of Fortimicin complex. The yield of the crude powder is about 35 g and the activity is 580 unit/mg (activity of 1 mg of the pure preparate corresponds to 1,000 units).

C. Isolation and purification of Fortimicin D

About 500 ml of silica gel is suspended in a solvent comprising isopropanol, chloroform, and concentrated aqueous ammonia (4:2:1 by volume) and packed in a glass column as a tight, uniform layer. Thereafter, the column is thoroughly washed with the same solvent. Then 10 g of the crude powder obtained in the above step B is charged over the silica gel to form a uniform, thin layer. After the crude powder is charged, the same solvent is poured gradually into the column from the top and thereafter elution is carried out continuously at a flow rate of about 50 ml/hour. The eluate is recovered in 20 ml fractions and each of the fractions is subjected to determination of activity by the paper disc method using *Bacillus subtilis* No. 10707. First, Fortimicin B is eluted followed by Fortimicin A. Then, the elution is continued and after Fortimicin C is eluted, Fortimicin D is eluted. The active fractions are subjected to thin layer chromatography and the fractions containing Fortimicin D are combined and concentrated under reduced pressure to sufficiently remove the solvent. The residue is dissolved in a small amount of water and the solution is freeze-dried to obtain about 1.5 g of a purified preparate of the free base of Fortimicin D. The product exhibits an activity of about 980 unit/mg.

D. Isolation and purification of Fortimicin KE

To obtain Fortimicin KE, 20 g of the crude powder obtained in the above step B is dissolved in 30 ml of water. The solution is adjusted to pH 7.5 with concentrated sulfuric acid and passed through a column packed with 1 L of cation exchange resin, Amberlite CG-50 (ammonium form). The effluent is discarded. The active substance is adsorbed on the resin. After washing the resin with water, elution is carried out with 0.2 N aqueous ammonia. The eluate is recovered in 50 ml fractions and each of the fractions is subjected to determination of activity by the paper disc method and thin layer chromatography.

First, several trace components are eluted. Thereafter, fractions containing Fortimicin KE and Fortimicin B are eluted. The fractions are combined and concentrated to 20 ml. The concentrate is freeze-dried to obtain 8 g of a crude powder.

About 500 ml of silica gel, suspended in a solvent comprising isopropanol, chloroform, and concentrated aqueous ammonia (4:2:1 by volume) is packed in a glass column as a tight, uniform layer. Thereafter, the column is thoroughly washed with the same solvent. Then the crude powder obtained above is charged over the silica gel in a uniform thin layer and the same solvent is poured gradually into the column from the top and thereafter elution is carried out continuously at a flow rate of about 50 ml/hour. The eluate is recovered in 20 ml fractions and each of the fractions is subjected to determination of activity by the paper disc method using *Bacillus subtilis* No. 10707. First, Fortimicin B is eluted followed by Fortimicin KE. The active fractions are subjected to thin layer chromatography and the fractions containing Fortimicin KE are combined and concentrated under reduced pressure to remove the solvent. The residue is dissolved in a small amount of water and the solution is freeze-dried to obtain about 2 g of a purified preparate of the free base of Fortimicin KE. The product exhibits an activity of about 970 unit/mg.

EXAMPLE 2

In this example, the strain used in the above Example 1 is used as the seed strain and the seed media (the first through fourth seed media) used in Example 1 are also used as the seed media. The fermentation medium utilized has the following composition:

| Soluble Starch | 4 g/dl |
|---|---|
| Ebios (dry yeast powder) | 3 g/dl |
| $K_2HPO_4$ | 0.05 g/dl |
| $MgSO_4 \cdot 7H_2O$ | 0.05 g/dl |
| KCl | 0.03 g/dl |
| $CaCO_3$ | 0.1 g/dl |

Fermentation is carried out under the same conditions as described in step A of Example 1 and a crude powder of Fortimicin complex is isolated in the same manner as described in step B of Example 1. As the result, about 71 g of the crude powder of Fortimicin complex exhibiting an activity of about 670 unit/mg is obtained. Then, 50 g of the crude powder is subject to purification according to the method described in the step C of Example 1. As a result, about 15 g of Fortimicin D exhibiting an activity of about 840 unit/mg is obtained.

For further purification, the preparate is subjected to cellulose column chromatography. About 500 ml of a cellulose powder (AVICEL, a produce of Funakoshi Seiyaku, K.K.) is suspended in a mixed solvent of n-butanol, acetic acid, pyridine and water (6:2:4:4 by volume) and packed in a glass column to form a tight, uniform layer. The column is then thoroughly washed with the same solvent. The preparate is charged over the cellulose powder to form a uniform, thin layer. After the preparate is charged, the same solvent is poured gradually into the column from the top and thereafter elution is carried out continuously at a flow rate of about 1 ml/min. The eluate is recovered in 10 ml fractions and each of the fractions is subjected to determination of activity by the paper disc method using *Bacillus subtilis* No. 10707. The active fractions are combined and concentrated under reduced pressure to sufficiently remove the solvent. The residue is dissolved in a small amount of water and freeze-dried. In this manner, about 8 g of a purified preparate of the free base of Fortimicin D exhibiting an activity of 970 unit/mg is obtained.

EXAMPLE 3

In this example, the procedure of Example 2 is repeated to obtain about 68 g of a crude powder of Fortimicin complex. Then 40 g of the crude powder is subjected to purification according to the method described in the step D of Example 1. As a result, 7 g of Fortimicin KE exhibiting an activity of about 860 unit/mg is obtained.

For further purification, the preparate is subjected to cellulose column chromatography. About 300 ml of a cellulose powder (AVICEL, a product of Funakoshi Seiyaku K.K.) is suspended in a solvent of n-butanol, acetic acid, pyridine and water (6:2:4:4 by volume) and packed in a glass column to form a tight, uniform layer. The column is then thoroughly washed with the same solvent. The preparate is charged over the cellulose powder to form a uniform, thin layer. After the preparate is charged, the same solvent is poured gradually into the column from the top and thereafter elution is carried out continuously at a flow rate of about 1 ml/min. The eluate is recovered in 7 ml fractions and each of the fractions is subjected to determination of activity by the paper disc method using *Bacillus subtilis* No. 10707. The active fractions are combined and concentrated under reduced pressure to remove the solvent. The residue is dissolved in a small amount of water and freeze-dried. In this manner, about 5 g of a purified preparate of the free base of Fortimicin KE exhibiting an activity of 980 unit/mg is obtained.

EXAMPLE 4

In this example, the strain used in the above Example 1 is used as the seed strain and the seed media (the first through fourth seed media) used in Example 1 are also used as the seed media. However, a fermentation medium having the following composition is used:

| Soluble starch | 4 g/dl |
|---|---|
| Casamino acid (an acid hydrolyzate of casein, product of Difco Laboratories, U.S.A.) | 3 g/dl |
| $K_2HPO_4$ | 0.05 g/dl |
| $MgSO_4 \cdot 7H_2O$ | 0.05 g/dl |
| KCl | 0.03 g/dl |
| $CaCO_3$ | 0.1 g/dl |

Fermentation is carried out under the same conditions as described in step A of Example 1 and Fortimicin D is isolated and purified in the same manner as described in the steps B and C of Example 1. As the result, about 15 g of purified preparate of Fortimicin D exhibiting an activity of about 975 unit/mg is obtained.

EXAMPLE 5

In this example, the procedure of Example 4 is repeated except that Fortimicin KE is isolated and purified in the same manner as described in steps B and D of Example 1. As the result, about 7 g of a purified preparate of Fortimicin KE exhibiting an activity of about 985 unit/mg is obtained.

EXAMPLE 6

In this example, *Micromonospora olivoasterospora* MK-70 (ATCC 21819), *Micromonospora olivoasterospora* MK-80 (ATCC 31010) and *Micromonospora olivoasterospora* Mm 744 (ATCC 31009) are used as the seed strains. The seed media (the first through fourth seed media) and the fermentation medium used in Example 1 are also used. Fermentation is carried out under the same conditions as described in the step A of Example 1 and Fortimicin D is isolated and purified in the same manner as described in the steps B and C of Example 1. Similarly, Fortimicin KE is isolated and purified in the same manner as described in steps B and D of Example 1. The yields and activities of the purified preparates of Fortimicin D and Fortimicin KE are shown in Table 5.

Table 5

| Fortimicin D | | |
|---|---|---|
| Strain | Yield (mg) | Activity (unit/mg) |
| *Micromonospora olivoasterospora* MK-70 | 450 | 985 |
| *Micromonospora olivoasterospora* MK-80 | 980 | 975 |
| *Micromonospora olivoasterospora* Mm 744 | 620 | 990 |

| Fortimicin KE | | |
|---|---|---|
| Strain | Yield (mg) | Activity (unit/mg) |
| *Micromonospora olivoasterospora* MK-70 | 300 | 985 |
| *Micromonospora olivoasterospora* MK-80 | 820 | 980 |
| *Micromonospora olivoasterospora* Mm 744 | 650 | 990 |

EXAMPLE 7

In this example, 10 g of the free base of Fortimicin D is dissolved in 500 ml of aqueous solution of saturated barium hydroxide. The solution is heated at a temperature of 100° C. for 3 hours and thereafter is allowed to stand until it is cooled to room temperature. The solution is neutralized with dry ice to precipitate the barium carbonate out. Filtration is carried out to remove the precipitate and the precipitate is washed with a small amount of water. The filtrate and the washings are combined and concentrated to about 20 ml. The concentrate is passed through a column packed with 500 ml of a cation exchange resin, Amberlite CG-50 (ammonium form). After the resin is washed with water, elution is carried out with 0.2 N aqueous ammonia. The eluate is recovered in 20 ml fractions and each of the fractions is subjected to determination of activity by the paper disc method. First, a small amount of reaction by-products is eluted. Thereafter, Fortimicin KE is eluted. Active fractions are subjected to thin layer chromatography and the fractions containing Fortimicin KE are combined and concentrated under reduced pressure to 20 ml. The concentrate is freeze-dried to obtain 7.8 g of the purified preparate of the free base of Fortimicin KE, the activity of which is about 970 unit/mg.

EXAMPLE 8

In this example, 1 g of the free base of Fortimicin D is dissolved in 5 ml of water. To the solution is added 1.7 ml of 6 N sulfuric acid. Then, 100 ml of methanol is added to the mixture to form a white precipitate. The precipitate is obtained by filtration and washed with methanol. After drying the precipitate under reduced pressure, 1.2 g of the sulfate of Fortimicin D exhibiting an activity of about 650 unit/mg is obtained.

EXAMPLE 9

In this example, 1 g of the free base of Fortimicin KE is dissolved in 5 ml of water. To the solution is added 2.0 ml of 6 N sulfuric acid. Then, 100 ml of methanol is added to the mixture to form a white precipitate. The precipitate is obtained by filtration and washed with methanol. After drying the precipitate under reduced pressure, 1.3 g of the sulfate of Fortimicin KE exhibiting about 610 unit/mg is obtained.

What is claimed is:

1. A compound of the formula:

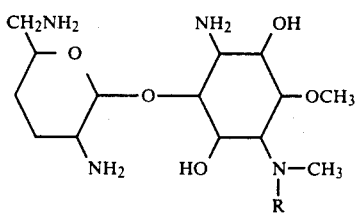

wherein R is H or

and the pharmaceutically acceptable non-toxic acid addition salts thereof.

2. A compound of the formula:

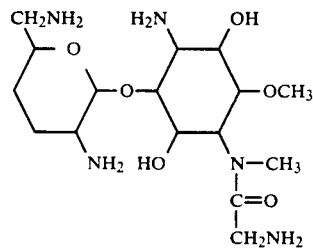

and the pharmaceutically acceptable non-toxic acid addition salts thereof.

3. A compound of the formula:

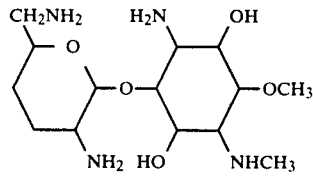

and the pharmaceutically acceptable non-toxic acid addition salts thereof.

* * * * *